(12) United States Patent
Stewart

(10) Patent No.: US 6,395,236 B1
(45) Date of Patent: May 28, 2002

(54) SYSTEM FOR TOBACCO SMOKE NEUTRALIZATION

(75) Inventor: Burch Stewart, Hialeah, FL (US)

(73) Assignee: Smoke B Gone, Inc., Pembroke Pines, FL (US)

( * ) Notice: Subject to any disclaimer, the term of this patent is extended or adjusted under 35 U.S.C. 154(b) by 0 days.

(21) Appl. No.: 09/236,597

(22) Filed: Jan. 26, 1999

Related U.S. Application Data

(60) Provisional application No. 60/072,857, filed on Jan. 28, 1998.

(51) Int. Cl.[7] .............................. A61L 9/01; A61L 13/00
(52) U.S. Cl. ............................... 422/123; 422/4; 422/5; 422/28; 422/125; 422/305; 424/76.2; 424/76.4; 131/220; 131/330; 131/290
(58) Field of Search ..................... 422/120, 28, 123, 422/4, 76.1; 131/330, 243, 290; 55/220; 424/76.1, 45

(56) References Cited

U.S. PATENT DOCUMENTS

| | | | | |
|---|---|---|---|---|
| 4,294,821 A | * | 10/1981 | Neumiller | 424/45 |
| 4,880,557 A | * | 11/1989 | Ohara et al. | 252/174.15 |
| 4,906,462 A | * | 3/1990 | Miki et al. | 424/76.1 |
| 5,534,229 A | * | 7/1996 | Nomura et al. | 422/123 |
| 5,591,395 A | * | 1/1997 | Schroeder et al. | 422/4 |
| 6,177,070 B1 | * | 1/2001 | Lynch | 424/76.1 |

* cited by examiner

*Primary Examiner*—Robert J. Warden, Sr.
*Assistant Examiner*—Sean E Conley
(74) *Attorney, Agent, or Firm*—M. K. Silverman; Yi Li

(57) ABSTRACT

A non-aerosol, non-wick pump spray system consisting of an emulsion of triethylene glycol in a range of about 0.5% to about 6.0% in distilled water, a surfactant such as sodium alkylbenzene sulfonate, and a suitable fragrance.

17 Claims, No Drawings

SYSTEM FOR TOBACCO SMOKE NEUTRALIZATION

REFERENCE TO RELATED APPLICATION

This Application corresponds in subject matter to Provisional Patent Application No. 60/072,857, filed Jan. 28, 1998.

BACKGROUND OF THE INVENTION

This invention relates to a formula and method of removing tobacco related odor from air and/or neutralizing the same.

It has long been known, as is exemplified by the applicable medical and environmental literature, that certain glycols may be employed in aerosols or vapor form in order to sterilize, that is, disinfect the air by killing airborne bacteria therein.

The similar objective is recited in U.S. Pat. No. 5,591,395 (1997) to Schroeder, entitled Method of Disinfecting Air. However, none of said prior art has specifically focused upon the problem of neutralizing cigarette, cigar or tobacco related odor in the air, that is, odor neutralization. Odor neutralization is generally accomplished through elastrostatic linking, that is, ionic bonding of a marketing agent to the odor causing molecules or particulates. In distinction, sterilization generally requires a chemical coaction, i.e., a covalent bonding to kill specific offending bacteria or de-activate an organic molecule or group thereof. Accordingly, to the knowledge of the within inventor, glycol vapors, including triethylene glycol vapors, have, in the prior art, only been used for purposes of disinfecting or sterilizing air, that is, not for the specific purpose of odor neutralization in which sterilization does not constitute a primary objective thereof. As such, there does not exist in the prior art any specific method of air sterilization in which the focus thereof is that of masking or neutralization of tobacco generated smoke odor.

SUMMARY OF THE INVENTION

The present invention comprises a non-aerosol, non-wick pump spray system consisting of an emulsion of triethylene glycol, a surfactant such as sodium ABS, and a fragrance such as vanilla/almond, all within distilled water.

It is an object of the invention to provide a pump spray delivered system of tobacco smoke odor neutralization.

It is another object to provide an improved and cost-effective means of removal of tobacco generated smoke odor from residential environments.

It s a further object to provide a means of the above type that will further sterilize air of any airborne bacteria which may be carried additionally by tobacco smoke generated molecules.

The above and yet other objectives and advantages of the present invention will become apparent from the hereinafter set forth Detailed Description of the Invention.

BRIEF DESCRIPTION OF THE DRAWINGS

There are no drawings in this application.

DETAILED DESCRIPTION OF THE INVENTION

As above noted, it is known that to accomplish odor removal, some form of sanitizing agent must be projected into the air in order to link with the odor causing particles.

Further, it is believed, that an agent, to be effective, must physically attach, and preferably envelope, to the odor causing particle. Therefore, any such odor neutralization system to be effective, must make use of a mechanism by which molecules of the active agent will attach and/or react with the odor generating molecules or particles to neutralize the same, either through chemical reaction, or by some mechanism, masking the odor generating aspect of such materials.

It has been found that certain glycols are capable of reacting with airborne bacteria and thereby destroying the health threatening function thereof. However, the within inventor has determined that the particular glycol known as triethylene glycol, when delivered in a suitable state of vaporization, will link with odor causing particles of tobacco-smoke based odors to mask the (as yet not fully known) odor causing mechanism of tobacco smoke. Accordingly, through the below set forth use of triethylene glycol as a smoke odor neutralizer, a substantial reduction, that is, neutralization, of odor as it can be detected by the human olfactory system, can be accomplished.

In that glycols are water soluble, distilled water has been selected as the primary carrier for the present system. In addition, a suitable surfactant is used to increase the solubility and dispersion of the glycol within the water used in the present system.

It has been found that the following formula, when used in a standard non-aerosol hand pump container, is capable of generating vapors and particulates of suitable size and concentration to attach to and, as above noted, suitably mask tobacco smoke generated odor.

The preferred embodiment of this formula is reflected in the following.

EXAMPLE:

(1) About 98% by weight distilled water was added to about 2% by weight of triethylene glycol. And (2) 1.6% by weight of sodium ABS surfactant to which was added about 0.04% by weight of a vanilla and almond fragrance.

It is believed that the percent of surfactant may be higher or lower depending upon the particular commercial grade surfactant which is utilized. Also, any of a number of other types of fragrances may be substituted, some of which will require a lesser, and other a greater, concentration to effect a desired end result. Further, the percent by weight of triethylene glycol may be in the range of about 0.5% to about 6.0%.

It is appreciated that the above system is not reliant upon any type of s not reliant upon any type of special wick, any aerosol delivery, any type of special purpose vaporizer, or any form of heating.

The percentage of triethylene glycol in the present system is much greater than that thought in the Example in regard to the above referenced patent to Schroeder.

It is also noted that in vapor delivered, means, millions of particles of the neutralizing product may be delivered, with a loss of mass, from the pump spray canister, winch is minuscule. Accordingly, for example hundreds of usages of a 100 gram container of the present system may be effected. also, such a pump spray canister will provide larger and wetter panicles than aerosol and other systems thereby enhancing system effectiveness.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth herewith.

Having thus described my invention, what I claim as new, useful and non-obvious and, accordingly, secure by Letters Patent of the United States is:

1. A tobacco smoke odor neutralization sprayer comprising:
   (a) a spray container with a non-aerosol spray pump, and
   (b) an aqueous composition consisting essentially of triethylene glycol in a concentration range from about 0.5% to about 6.0% (w/w) in water for neutralizing tobacco smoke odor when sprayed from the spray container.

2. The tobacco smoke odor neutralization sprayer of claim 1, wherein said water is distilled water.

3. The tobacco smoke odor neutralization sprayer of claim 1, further consisting essentially of a surfactant.

4. The tobacco smoke odor neutralization sprayer of claim 3, wherein said surfactant is sodium alkylbenzene sulfonate.

5. The tobacco smoke odor neutralization sprayer of claim 1, further consisting essentially of a fragrance.

6. The tobacco smoke odor neutralization sprayer of claim 1, wherein said triethylene glycol is in a concentration of about 2.0% (w/w).

7. A non-wick, non-aerosol pump spray composition for spraying to neutralize tobacco smoke odor consisting essentially of:
   an aqueous composition of triethylene glycol in a concentration range of about 0.5% to 6.0% by weight in distilled water, and a surfactant.

8. The composition of claim 7, wherein said surfactant is sodium alkylbenzene sulfonate.

9. The composition of claim 7, wherein said triethylene glycol is in a concentration of about 2% (w/w).

10. The composition of claim 7, further consisting essentially of a fragrance.

11. A method of neutralizing tobacco smoke odor comprising:
    using a sprayer having a non-aerosol spray pump to spray an aqueous composition consisting essentially of triethylene glycol into air containing tobacco smoke odor to neutralize said tobacco smoke odor.

12. The method of claim 11, wherein said aqueous composition of triethylene glycol is in a concentration range from about 0.5% to 6.0% (w/w) in water.

13. The method of claim 12, wherein said water is distilled water.

14. The method of claim 12, wherein said aqueous composition of triethylene glycol further consisting essentially of a surfactant.

15. The method of claim 14, wherein said surfactant is sodium alkylbenzene sulfonate.

16. The method of claim 12, wherein said aqueous composition of triethylene glycol further consists essentially of a fragrance.

17. The method of claim 12, wherein said triethylene glycol is in a concentration of about 2.0% (w/w).

* * * * *